United States Patent [19]

Altman et al.

[11] Patent Number: 5,583,049
[45] Date of Patent: *Dec. 10, 1996

[54] CONTROL OF LOW INVENTORY ALKYLATION UNIT

[75] Inventors: Lawrence J. Altman, Cherry Hill; Rafi Jalkian, Mantua, both of N.J.

[73] Assignee: Mobil Oil Corporation, Fairfax, Va.

[ * ] Notice: The term of this patent shall not extend beyond the expiration date of Pat. No. 5,407,830.

[21] Appl. No.: 423,336

[22] Filed: Apr. 17, 1995

Related U.S. Application Data

[63] Continuation-in-part of Ser. No. 160,565, Dec. 1, 1993, Pat. No. 5,407,830.
[51] Int. Cl.$^6$ ................................................. G01N 21/35
[52] U.S. Cl. ................ 436/55; 250/339.08; 250/339.11; 250/399.12; 356/346; 422/67; 422/68.1; 422/82.05; 422/111; 436/60; 436/61; 436/139; 436/171; 585/725
[58] Field of Search ............................ 422/108–111, 67, 422/68.1, 82.05; 436/55, 60–61, 139, 171; 250/341, 339.12, 339.08, 339.11; 356/346; 585/725

[56] References Cited

U.S. PATENT DOCUMENTS

| | | | |
|---|---|---|---|
| 4,205,196 | 5/1980 | Makovec et al. | 422/111 X |
| 4,207,423 | 6/1980 | Makovec et al. | 422/111 X |
| 4,276,257 | 6/1981 | Dixon et al. | 422/62 |
| 4,543,237 | 9/1985 | Webb et al. | 422/62 |
| 4,677,244 | 6/1987 | Hachmuth et al. | 422/111 X |
| 4,707,603 | 11/1987 | Miemela et al. | 250/339.08 |
| 5,073,674 | 12/1991 | Olah | 585/709 |
| 5,145,785 | 9/1992 | Maggard et al. | 436/8 |
| 5,407,830 | 4/1995 | Altman et al. | 436/55 |

OTHER PUBLICATIONS

Katlafsky et al., Attenuated Total Reflectance Infrared Analysis of Aqueous Solutions, 35, Anal Chem, Oct. 1963, pp. 1665–1670.

Simphany et al., Fourier Transform Infrared Spectra of Organic Compounds in Solution and as Thin Layers obtained by Using an Attenuated Total Internal Reflectance Fiber Optic Cell, analytical Chemistry, 1988, 60, pp. 1908–1910.

Zhaohul et al., Use NIR Spectroscopy for On–line Gasoline Analysis, Hydrocarbon Processing, Jan. 1992, pp.92–96.

*Primary Examiner*—Jill Warden
*Assistant Examiner*—Harold Y. Pyon
*Attorney, Agent, or Firm*—Ronald A. Bleeker; Malcolm D. Keen; Gerry L. Harris

[57] ABSTRACT

A method and system for controlling an HF alkylation system comprising a reactor, a settler, an HF acid regenerator and a source of fresh HF acid wherein a stream of olefins and a stream of isobutanes are contacted in the reactor in the presence an HF acid catalyst. At least the reactor feed is sampled, and the sample is passed to an analyzer using an attenuated total reflectance cell. Signals are generated which are representative of infrared spectra of the samples in a range providing information on the amount of at least one of HF, water, ASO and sulfolane. These signals are simultaneously determined and generated because all absorb in the same spectral region. This aspect provides for viewing these distortions of the main HF absorption band to quantify these three components. The infrared spectra signals are compared with stored signals to generate control signals; and at least one of HF, water and sulfolane fed to the reactor feed is adjusted in response to the control signal.

19 Claims, 6 Drawing Sheets

5,583,049

CONTROL OF LOW INVENTORY ALKYLATION UNIT

CROSS REFERENCE TO RELATED APPLICATION

This application is a continuation-in-part of U.S. patent application Ser. No. 08/160,565, filed Dec. 1, 1993, now U.S. Pat. No. 5,407,830. U.S. patent application Ser. No. 08/160,565, filed Dec. 1, 1993 is hereby incorporated herein by reference.

BACKGROUND OF THE INVENTION

The present invention relates to a liquid acid catalyzed alkylation unit. More specifically, the present invention relates to the in situ measurement and the control of a low inventory liquid acid catalyzed alkylation unit.

Alkylation is a reaction in which an alkyl group is added to an organic molecule. Thus, an isoparaffin can be reacted with an olefin to provide an isoparaffin of higher molecular weight. The process depends on the reaction of a $C_2$ to $C_5$ olefin with isobutane in the presence of an acidic catalyst producing an alkylate. This alkylate is a valuable blending component in the manufacture of gasolines due not only to its high octane rating but also its sensitivity to octane enhancing additives.

U.S. Pat. No. 4,795,728 discloses a hydrofluoric acid (HF) catalyzed alkylation process for producing motor fuel. The hydrofluoric acid catalyst complex contains from 0.5 to 5 weight percent of a cationic or anionic surfactant component enabling the process to be operated at an olefin acid volumetric feed ratio of greater than 1.0 while maintaining acceptable alkylate quality.

For a general discussion of sulfuric acid alkylation, see the series of three articles by L. F Albright et. al., "Alkylation of Isobutane with $C_4$ Olefins", 27 Ind. Eng. Chem. Res, pgs. 381–397 (1988). HF alkylation is described in further detail in the Handbook of Petroleum Refining Processes, pgs. 3–28 (1986).

Generally, in acid alkylation longer residence times for the hydrocarbon/acid contact are preferred. However, longer residence times result in reduced reactor capacity as well as increased operating costs. For a discussion of residence time see Albright, "Modern Alkylation", Oil and Gas Journal, p. 83, (Nov. 12, 1990).

Lewis acids are reducing acids having a high vapor pressure, and a propensity to flash into a cloud. Lewis acid catalyzed alkylation processes are also currently used to produce high octane blending components. Examples of Lewis acids include $BF_3$, $AlCl_3$ and $SbF_3$.

Liquid acid catalyzed continuous alkylation processes generally comprise a reactor, a settler where hydrocarbon droplets are separated from the acid and a heat exchanger where the heat generated by the exothermic reaction is removed. Each vessel requires a large liquid acid catalyst inventory.

Both sulfuric acid and HF alkylation share inherent drawbacks including environmental and safety concerns and acid consumption. While catalyst complexes comprising $BF_3$ overcome some of the safety and environmental drawbacks of sulfuric acid and HF alkylation systems, the volume and quality of $BF_3$ alkylates have not, proven comparable to that of sulfuric or HF alkylates. Currently HF catalyzed alkylates processes are under particular safety and environmental scrutiny, because of the toxic and corrosive nature of HF.

U.S. Pat. Nos. 4,938,935 and 4,938,936 describe the danger of HF leaks. Through many safety precautions are taken to prevent leaks, massive or catastrophic leaks are feared primarily because the anhydrous acid will fume on escape crating a vapor cloud that can be spread for some distance.

It is therefore an object of the present invention to provide a method and system for reducing the liquid acid catalyst inventory in acid catalyzed continuous alkylation processes.

It is a further object to provide a method and system for improving the safety of liquid acid catalyzed continuous alkylation.

It is a further object of the present invention to provide a method and system for minimizing the risk of a sudden release of toxic material.

SUMMARY OF THE INVENTION

The on-line analyzer of the present invention provides for fast and accurate control of the potentially fast changing catalyst composition in a low inventory HF alkylation process. The ability to provide rapid corrective control of the catalyst composition in accordance with the present invention is essential to the use of a low inventory catalyst system because without the buffer provided by a standard inventory the system is subject to large swings.

A significant aspect of the present invention is that HF, water and sulfolane are simultaneously determined because essentially all absorb in the same spectral region. Thus, the method and system provide for viewing these distortions of the main HF absorption band to quantify these three components.

In accordance with a broad aspect of the present invention there is provided a method of and system for controlling an HF alkylation system comprising a reactor, a settler, an HF acid regenerator and a source of fresh HF acid. A stream of olefins and a stream of isobutanes are contacted in the reactor in the presence an HF acid catalyst. The reactor provides a combined hydrocarbon and HF acid output stream to the settler wherein separation provides an alkylate laden hydrocarbon product stream and a separated HF acid stream. The product stream is further processed to remove non-alkylate components therefrom, and a minor portion of the separated HF acid stream is fed to the acid regenerator. A major portion of the separated HF acid stream is returned to the reactor along with fresh HF acid from the acid source and regenerated HF acid from the regenerator. The invention includes sampling at least the reactor acid feed stream, and passing the samples to a analyzer using an attenuated total reflectance cell. Signals are generated representative of infrared spectra of the samples in a range providing information on the amount of at least one of HF, water, ASO (acid soluble oils) and sulfolane being fed to the reactor. The infrared spectra signals are compared with stored signals to generate control signals and the HF, water, ASO and sulfolane in the reactor feed are adjusted in response to the control signals.

In accordance with a specific aspect of the invention, there is provided a method and system for controlling a low inventory alkylation unit by sampling at least the reactor feed and passing the samples to an attenuated total reflectance cell of an analyzer including a spectroscope, e.g. a fourier transform infrared spectrometer (FTIR). The temperature of the samples are regulated to that of calibration standard temperature upon which a model was built. Signals are generated which are representative of reference and measured spectra for at least one of HF, water, ASO, and an additive, e.g. sulfolane, for reducing the vapor pressure of the HF acid. The spectra signals are processed to correct for instrumental variation in accordance with:

$$A_{corr} = \log_{10}\{S_o/S[R_o/R]\};$$

wherein $A_{corr}$=corrected sample absorbance spectrum;
S=current sample single beam spectrum;
$S_o$=sample single beam spectrum obtained at time 0 with an empty cell;
R=current reference cell single beam spectrum; and
$R_o$=reference cell single beam spectrum obtained at time 0.

Then a derivative is generated of the corrected sample absorbance spectrum, and the derivative is normalized in accordance with:

$$D_{norm} = D_i / \sum_{2250}^{3950} |D_i|;$$

wherein $D_{norm}$=normalized derivative spectral element; and
$D_i$=derivative spectral element.

Stored model vectors are multiplied by the normalized derivative spectral elements to obtain values indicative of amount of the monitored at least one of water, ASO, HF, and additive. The values, which may be percent of HF catalyst, are compared to reference values to obtain difference signals, and the flow of the monitored at least one of water, ASO, HF, and additive is controlled in response to said difference signals.

DESCRIPTION OF SPECIFIC EMBODIMENTS

Figure 1:
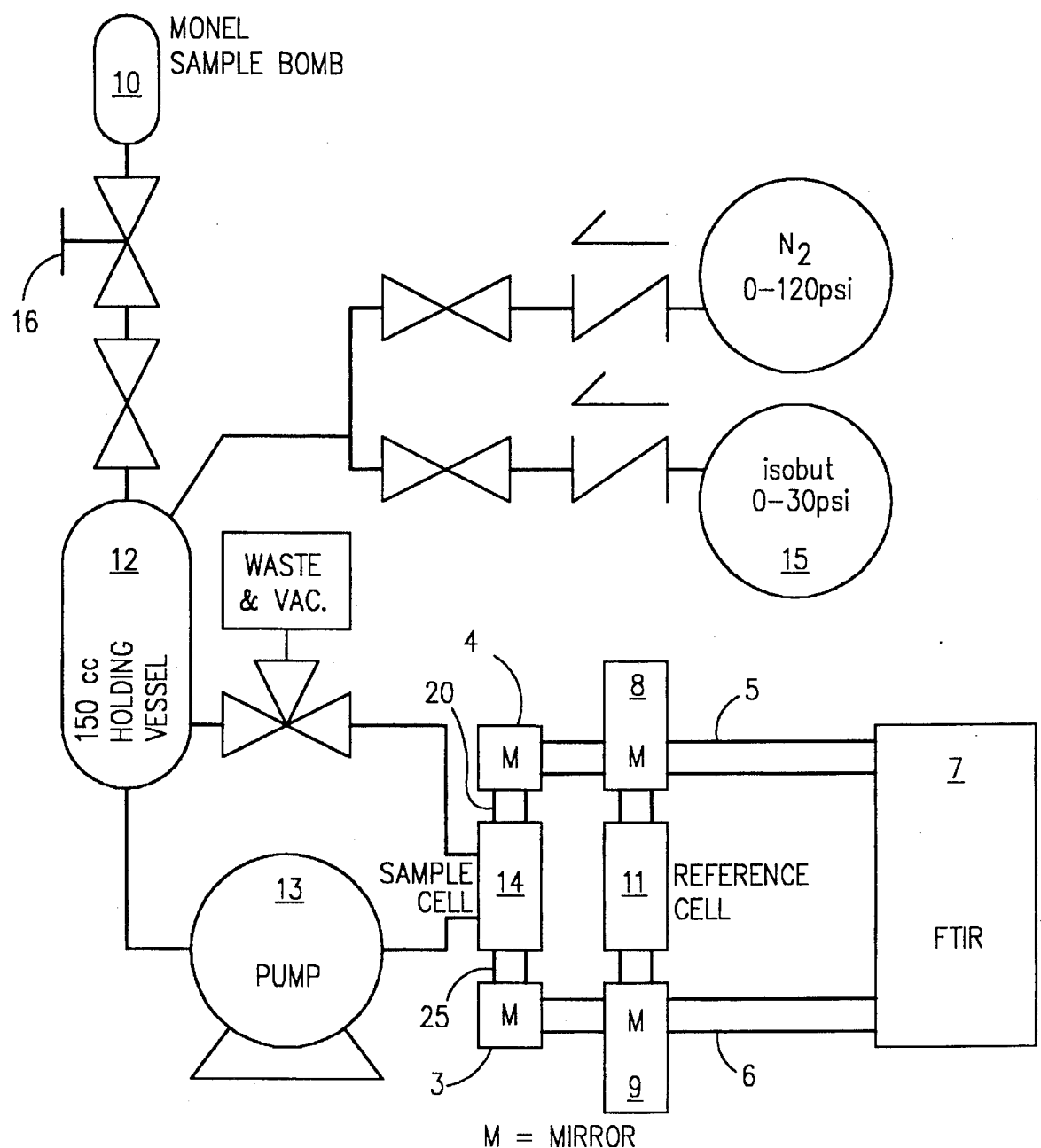
FIG. 1 is a block diagram of an on-line FTIC analyzer embodiment used in the present invention.

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2 methyl butane, 2 methylhexane, 2,3-dimethylbutane and 2,4-dimethylhexane.

The olefin component of the feedstock includes at least one olefin having from 2 to 12 carbon atoms. A few representative examples of such olefins include butene-2, isobutylene, butene-1, propylene, ethylene, hexene, octene and heptene. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 the disclosure of which is incorporated herein by reference.

The molar ratio of isoparaffin to olefin is generally from about 1:1 to about 100:1 preferably from about 1:1 to about 50:1, and more preferably from about 5:1 to about 20:1.

The present alkylation process is suitably conducted at temperatures from about −30° C. to about 200° C., preferably from about 0° C. to about 100° C., and more preferably below about 50° C. to avoid undesirable side reactions. Lower reaction temperatures are preferred to maximize alkylate octane. Lower temperatures are generally preferred, for example temperatures as low as 0° C. may be effectively employed. Operating temperature typically falls within the range of from about 0° C. to about 50° C., with the most preferred operating temperatures falling within the range of from about 20° C. to about 30° C.

Operating pressure is controlled to maintain the reactants in the liquid phase, and is suitably from about 50 psig to about 1500 psig. Preferably, the pressure is from about 75 psig to about 250 psig. The catalyst weight hourly space velocity as well as the acid dosage varies with the particular acid catalyst system employed.

The particular operating conditions used in the present process will depend on the specific alkylation reaction being effected. Process conditions such as temperature, pressure, space velocity and molar ratio of the reactants will affect the characteristics of the resulting alkylate, and may be adjusted within the disclosed ranges.

Thus, the reduction of HF inventory substantially enhances environmental safety. However, operation with low inventory requires a preparedness for system upset with an ability to rapidly quantify direction and rate of upset and to quickly respond to offset the conditions causing the upset. Accordingly, operation of a standard HF alkylation unit with a low HF inventory requires a very rapid response system for controlling low HF inventory systems as provided in accordance with the present invention. It is also essential to control the amount of water and the HF sulfolane content in a low HF inventory unit in order to prevent corrosion.

An advantage of the instant invention is that the system obviates the need and the inherent risk of taking HF samples and bringing them back to a laboratory. Corrosion in an HF alkylation system is largely from iron fluoride deposition and stress corrosion. HF attacks the slag formations in welds, and process vessels must therefore be stress relieved. Also, any part of the system that is in direct contact with HF should be made of monel metal or other corrosion resistant substance.

With reference to FIG. 1, there is shown an on-line FTIR analyzer for the on-line prediction of HF, water, and sulfolane in a low inventory HF alkylation catalyst system. This analyzer satisfies the need generated by lower inventory HF alkylation with a rapid, continuous method of analyzing HF, water, and sulfolane to control the process. The system provides these measurements with spectroscopic on-line HF catalyst composition analysis.

Sapphire in the cell 14 is the optical internal reflectance element (IRE) in contact with the HF catalyst. Sapphire was found to be an acceptable material due to its corrosion resistance. Sapphire is optically useful from the UV to IR. A thermo-electrically (TE) cooled lead selenide (PbSe) detector is used because its responsivity matches the transmission of sapphire in terms of low wave number cutoff, and because it is about 4 times more sensitive than a TE cooled deuterated triglycine sulfate (DTGS) detector in this region.

Standard sample preparation consisted of weighing appropriate amounts of water, sulfolane, and acid soluble oils (ASO—from a refinery) into a 150 cc Monel bomb 10. A valve was then attached to the bomb for HF addition. A measuring tube constructed from Monel and equipped with a Teflon sight tube was filled with HF to a needed height from an inverted No. 4 HF (for liquid HF transfer) cylinder. The HF was then injected into the bomb 10. The overall mass of the solution was prepared to be about 130 g and was accurately determined by weighing the bomb after HF addition. The contents of the bomb were introduced into the sample loop by inverting the bomb 10 and allowing the contents to flow into an evacuated circulation loop defined by valve 16 holding vessel 12, pump 13, sample cell 14. The solution was then circulated at a rate of 0.5 gpm in a temperature controlled (73° F.) loop containing the sapphire cell 14. In an effort to simulate anticipated conditions of the unit catalyst, the solution in the loop was equilibrated with isobutane from a source 15 at 25 psig for 15 minutes before the start of spectral acquisition. Acquisition of the sample spectrum and the reference cell spectrum consisted of coadding 64 scans at 8 cm$^{-1}$ resolution and utilizing the 4100 to 2100 cm$^{-1}$ region.

Two light pipes 5,6 interconnect the FTIR analyzer 7 with a pair of mirrors 8,9. The light pipes are purged to exclude water vapor and carbon dioxide. Infrared (IR) light from the FTIR 7 passes down one of the light pipes 5 to a multiplexing mirror 8. The mirror moves into and out of the IR beam. When in the beam of light, the mirror diverts the beam of light into a reference cell 11. The beam exits the reference cell 11, and is again diverted by another multiplexing mirror 9 into the light pipe 6 and back to the detector portion of the FTIR 7 where the light signal is converted into an electrical signal. When the mirrors 8,9 are not in the beam of IR light, the light passes to another mirror 4 where it is diverted into the sample cell 14, out of the cell 14 and diverted by yet another mirror 3 to return by light pipe 6 to the FTIR 6 where at least one sample signal is generated. The sample cell 14 is shown in greater detail in FIG. 3.

Figure 2:
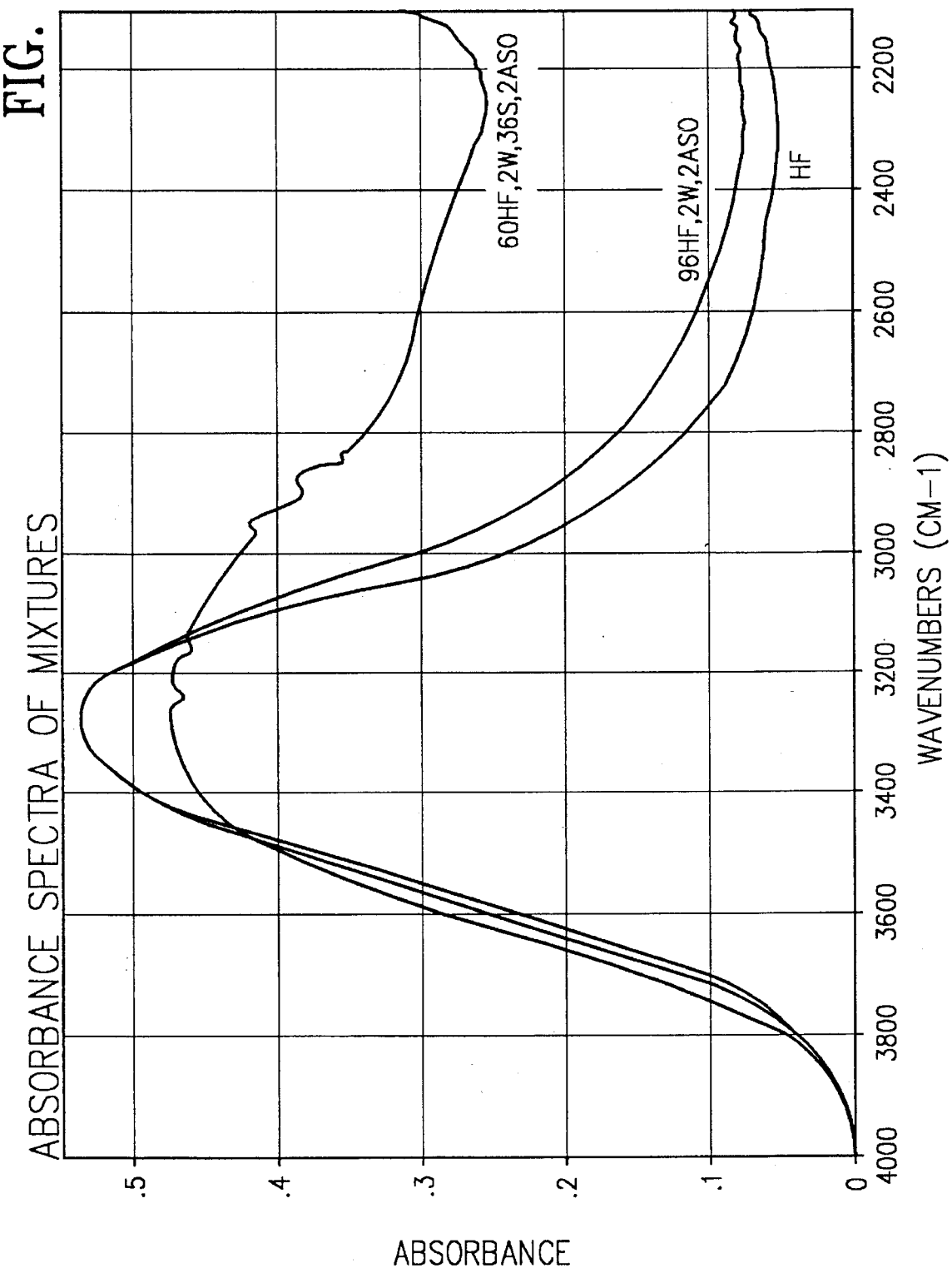
FIG. 2 is a graph of the main absorption band used in the present invention.

With reference to FIG. 2, the main absorption band in the region between 4100 and 2100 cm$^{-1}$ is due to HF. Water and sulfolane modify the absorption spectrum of HF and they form a wide HF-water-sulfolane polymer band at lower wave numbers. ASO in samples could be analyzed by use of the C-H absorption bands around 3000 cm$^{-1}$. However, both sulfolane and isobutane also have C-H absorption bands around 3000 cm$^{-1}$ which may interfere with a possible ASO determination.

A calibration set was prepared using statistical experimental design. The set covers catalyst composition containing 100 to 50% HF, 0 to 10% water, 0 to 50% sulfolane, and 0 to 10% ASO. This set which consists of 70 standards includes anticipated catalyst compositions.

The calibration model was created in array basic with the aid of Lab Calc PLS (partial least squares) algorithm manufactured by Galactic Industries Corp. A computer program listing for MHF-Continuous Refinery Acid Prediction Program is in an appendix to this specification.

The raw single beam spectra of the sample was first corrected for instrumental variations alone as shown in Equation 1.

$$A_{corr} = \log_{10}\{S_o/S[R_o/R]\}; \quad [Eq. 1]$$

wherein $A_{corr}$=corrected sample absorbance spectrum;

S=current sample single beam spectrum;

$S_o$=sample single beam spectrum obtained at time 0 with an empty cell;

R=current reference cell single beam spectrum; and $R_o$=reference cell single beam spectrum obtained at time 0.

Correction for the ATR crystal transmission variation as a function of time is not needed because no changes in the ATR crystal transmission were observed over a period of a few months. The first derivative of corrected absorption spectrum was then obtained with a 13 point Savisky-Golay smoothing function. The first derivative and smoothing eliminated baseline shifts and very low frequency variations. The derivative spectrum between 3950 and 2250 cm$^{-1}$ was then normalized by Equation 2 to correct for variations in absorption intensity.

$$D_{norm} = D_i / \sum_{2250}^{3950} |D_i|; \quad [Eq. 2]$$

wherein $D_{norm}$=normalized derivative spectral element; and $D_i$=derivative spectral element.

Variations in the intensity are due to changes in the penetration of the IR beam into the solution due to changes in refractive index caused by the addition of sulfolane and ASO. Addition of sulfolane and ASO greatly modify the refractive index of HF/water. In addition, the chemical interaction of HF with water as well as sulfolane is strongly dependent on temperature. Therefore, the model includes temperature dependence. Spectral normalization reduces the standard error of prediction (SEP) by a factor of 15% and the calibration model is less susceptible to temperature variations.

Partial least squares and principal component regression (PCR) methods were used to build calibration models using different bands of the spectra. Limited region models were evaluated utilizing the band between 3950 and 3000 cm$^{-1}$ to predict HF, water, and sulfolane. Another model was evaluated utilizing the band between 3000 and 2800 cm$^{-1}$ to predict sulfolane and ASO, and the region between 2800 and 2200 cm$^{-1}$ was evaluated for water prediction. The best overall model was achieved by using the whole range between 3950 and 2250 cm$^{-1}$.

The PLS method was found to be superior to the PCR method in terms of SEP (by a factor of 100%). This might be explained by the fact PCR is better able to model partially nonlinear calibration sets. The nonlinearity is due to large changes in penetration depth of the evanescent IR wave resulting from variations in the refractive index of varying concentrations. The normalization function of Equation 2 is a rectangular function.

Although 70 calibration spectra were obtain over a span of three months, the long term stability of the model as well as the cell were evaluated by continuously circulating a standard over a period of 45 hours and predicting the composition every fifteen minutes as it would be done in the field. It appears that the actual spectra of the solution changes as a function of time (HF and water prediction decreases and sulfolane prediction increases) and then reaches a steady state condition after about ten hours on stream. This effect may be explained as corrosion of the loop, or that isobutane saturation is slower than first believed, or possible protonation and subsequent addition of water to ASO.

Calibration and prediction of ASO was attempted, but since the sulfolane and isobutane C-H bands overlap with the ASO C-H bands, error in ASO prediction was too large to be useful (ASO prediction RMS error of 1.3% with samples containing 0 to 10% ASO). The errors in ASO prediction are due to many factors including errors in the composition of standards due to preparation and carry over in the circulation loop, nonlinearity of the measurement due to changes in refractive index of the solution, and errors inherent using the ATR method itself.

Comparisons of characteristics of the samples with those of previous samples from the same location are made to determine significant trends or abnormal conditions. By comparing current trends of the samples against these reference trend values, abnormal trends can be detected and corrective action can be taken.

The system is able to measure the effects of small percentage amounts of water in the spectra of the sampled stream. This measurement is made by identifying small differences in spectra which corresponds to small water changes. Thus, the system is able to reproducibly determine small amounts of water. Monitoring and controlling water in the system is critical, because too much water will stop the process, and too little water will cause serve corrosion of carbon steel.

Figure 3:
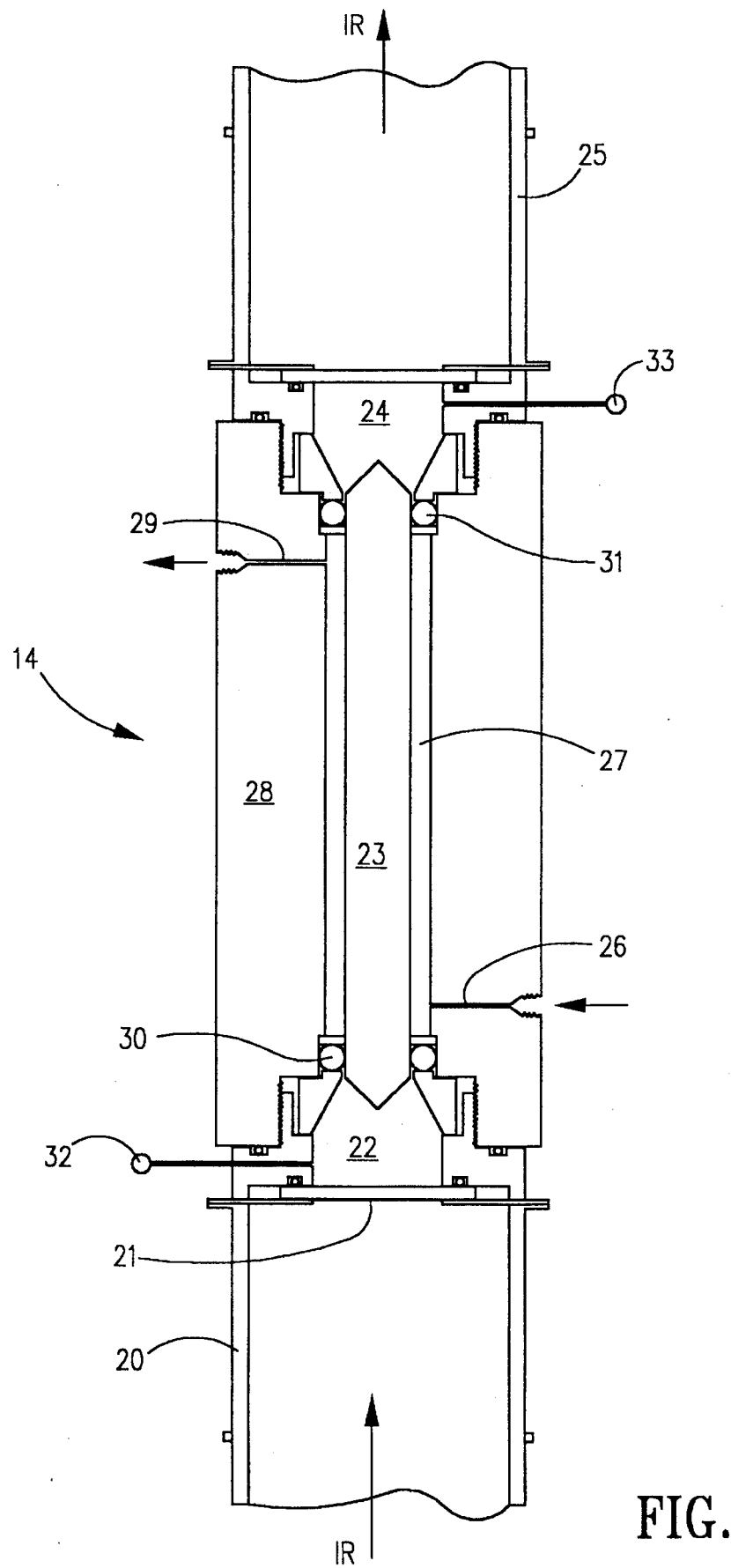
FIG. 3 is a cross-sectional view of an attenuated total reflectance cell embodiment of the present invention.

The normal IR sampling method using transmission through thin films (on the order of a few microns) would pose great difficulty and problems with the alkylation catalysts because corrosion particles would clot or plug the system. An attenuated total reflectance (ATR) cell as shown in FIG. 3 was chosen to overcome sampling problems. In an ATR cell, the light reflected back from the internal surface of the crystal establishes a standing wave at the surface of the crystal into the phase in contact with the crystal. The amplitude of the electric field of the standing wave decreases exponentially with distance from the surface of the crystal. The distance where the field amplitude equals 1/e (e=2.718) of the initial magnitude is defined as the penetration depth or sampling distance. The overall sampling depth depends on the wavelength, the refractive index of crystal as well as the sample, light incidence angle, and the number of reflections. ATR measurements are sensitive to degradation of and deposit formation on the crystal surface. Therefore, the crystal surface should be regularly cleaned, for example daily, by flushing with HF.

With reference to FIG. 3, the IR beam of light passes through a light pipe portion 20, through a sapphire window 21 and is focused into the mirror in a secondary containment area 22. The light then enters a sapphire rod 23 where the light passes through internal reflections. The light exits through another secondary containment area 24, another sapphire window 25, down a light pipe 25 and returns to the FTIR 7 as described with reference to FIG. 1. A sample enters the cell 14 through a line 26, and into an annular sample area 27 formed between the sapphire rod 23 and the Monel cell housing 28, and exits the cell through a line 29. A portion of the IR light enters the sample area 27 and interacts with the sample therein to give a light signal representative of absorption.

Each of the secondary containment areas 22,24 is in fluid communication with an O-ring 30,31 such that in the event of a leak through an O-ring 30, 31 the leak would be confined to one of the secondary containment areas. Further, a signal representative of such leak would be given by a change in the IR beam. Another leak signal would also be given by a pressure switch 30,31 which is responsive to an increase in pressure in a respective containment area 22,24.

The method and system of the present invention provides an analyzer for measurement of the composition of the acid, and controlling the amount of fresh acid and/or the amount of water brought to the unit. Also, the measurements permit the reduction of feedback from the regenerator so that it is possible to enhance the removal and disposed of ASO. Thus, the analyzer will provide a continuing capacity to adjust the composition of the catalyst to permit operation in an optimum operating region. Such close control of the acid composition will avoid the possibility of runaway condition, minimize the possibility of corrosion in the unit, and ease compliance with requirements to use an amount of additive, such as sulfolane, to reduce the vapor pressure of the acid.

Figure 4:
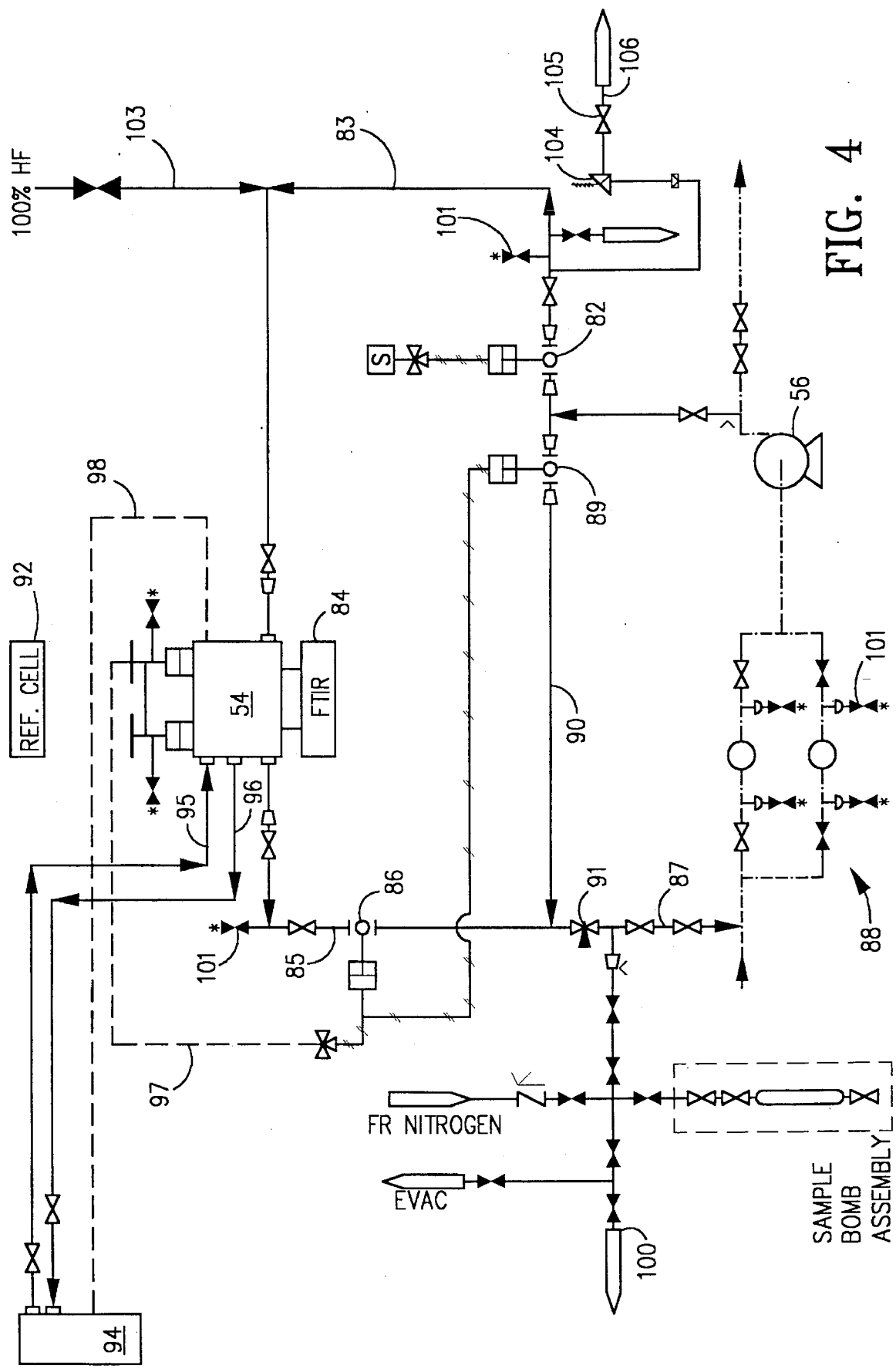
FIG. 4 shows a sampling flow diagram interconnecting a reactor unit and FTIC in accordance with the present invention.

With reference to FIG. 4, a slip-stream sampling loop is formed about a main catalyst pump 56 in an alkylation unit. Starting with the pump 56 the sampling loop includes a valve 82, a line 83 to a sample cell 54 where there are two manually operable valves 110, 41 to open the loop when needed. The loop also includes a line 85 to a valve 86, then a line 87 to a manual sample acquisition unit 88 and then back to the intake of the pump 56. The manual sampling acquisition unit 88 permits manually sampling of the catalyst which is analyzed manually and checked versus the response of the on-line analyzer.

The system also includes a pump 89, a line 90 and the line 87 to provide a bypass loop of the cell 54 when in a bypass mode. The sampling loop also includes a needle valve 91 to adjust the flow of the catalyst through the sampling loop.

The system includes a FTIR spectrometer 84 such as a Spectra-Tech Applied Systems MonitIR. The system also includes a reference cell 92 which is not connected to the sampling system, but is provided for comparison and corrections for variations of the FTIR instrument. The FTIR and cells are connected and function as described hereinabove with reference to FIGS. 1 and 3.

A bath 94 is provided which functions as a temperature control unit. The bath 94 has insulated lines 95,96 extending through the jacket of the cell 54, to regulate the temperature of cell body. Purge line 97,98 are provided to remove water vapor and carbon dioxide from the light pipe connecting the FTIR to the sample cell 54. The system also includes a temperature probe or transducer, and a pressure sensor. The cell 54 has a secondary barrier to indicate leaks from the main barrier, and includes a pressure switch.

Further, there is provision to isolate the sampling loop and drain out the acid through a valve 100. Thus, when there is need to service the line, the acid can be drained. A vacuum line is connected to the valves 101 (marked with a asterisk) to evacuate the remaining acid. There is also a provision via line 103 to introduce 100% anhydrous acid to wash out the cell 54 which travels from an anhydrous HF tank to the cell 54 and back through valve 86 and into the main pump 56. As a safety provision, there is also provided on the line a rupture disk 104 set at about 300 pounds, which is connected to a relief valve 105 connected to a line 106 for full evacuation of the acid. The cell is tested at about 500 pounds, and then there is provided a safety rupture disk 104 that is set at 300 pounds to prevent any major upsets, destruction of the cell, or release to the atmosphere.

Figure 5:
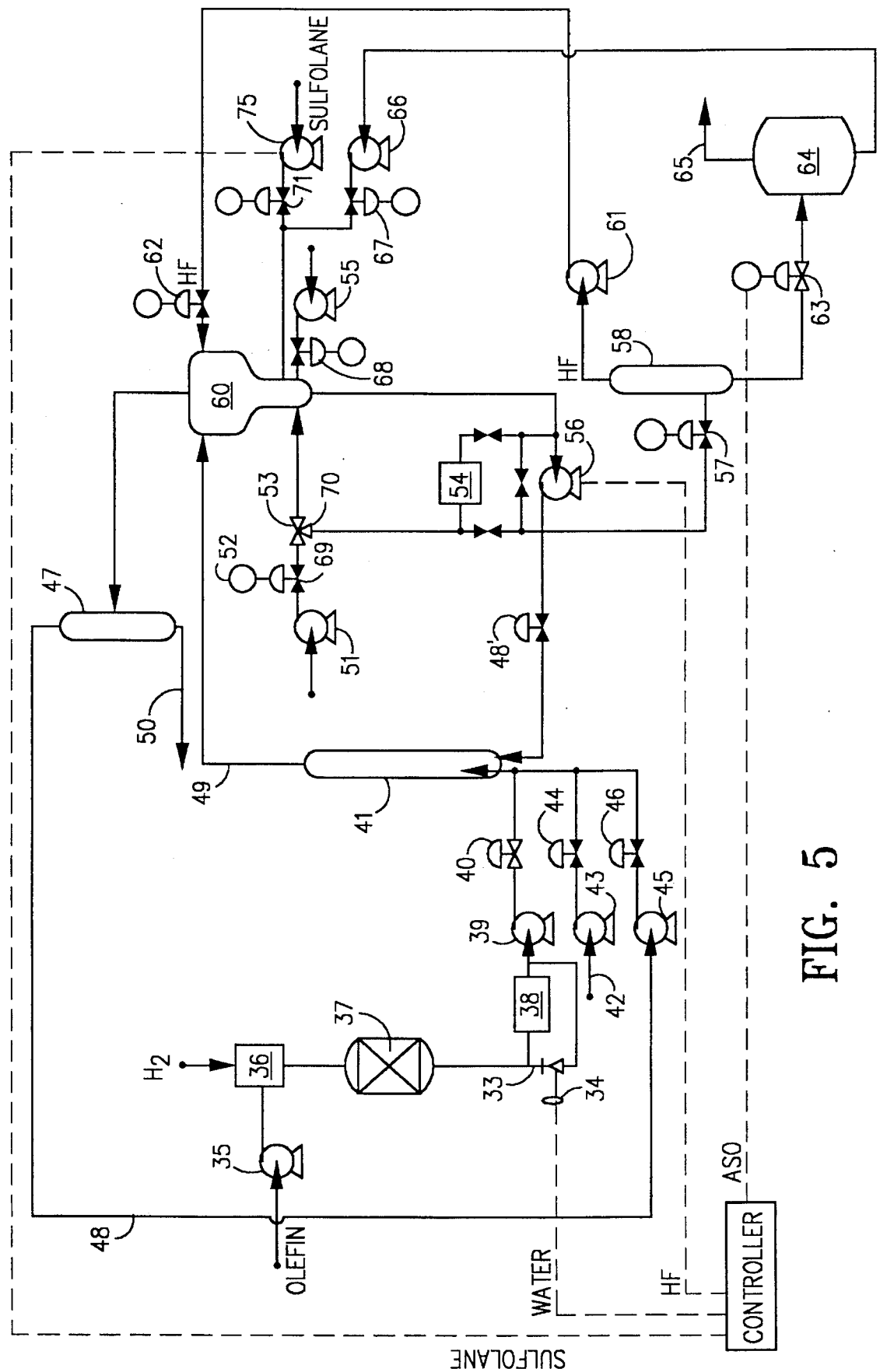
FIG. 5 is a control flow diagram for an HF alkylation unit in accordance with the present invention.

With reference to FIG. 5 there is shown an HF alkylation catalyst control flow diagram of an embodiment of the present invention. Olefin feed is passed by a pump 35 to a mixer 36 where hydrogen is added to the feed prior to introduction to a hydrotreater 37. The hydrotreater 37 converts diolefins or dienes to single double bonds. A dryer 38 is provided to remove any excess water provided with the feed over which the system would have no control, and which might present a potential upset. A bypass line 33 having a control valve 34 response to the water control signal bypasses the dryer 38, and thereby provides a capacity to increase the water content. After the dryer 38 the olefin feed is passed by a pump 39 through a control valve 40, and into a riser reactor 41. This feed is also mixed with a source of isobutane provided by a line 42 entering through pump 43 and a control valve 44. Valves 40 and 44 adjust the isobutane to olefin ratio to provide an optimum mixture of reactants.

A pump 45 feeds isobutane recovered via line 48 from an alkylation accumulator unit 47. Thus, feed excess isobutane that was recovered by the accumulator 47 is fed back through a control valve 46. The reactants enter the riser reactor 41 and the acid catalyst enters the reactor 41 through a main catalyst pump 56 and a control valve 48. From the riser reactor 42, the reactants, the products and the catalyst are passed by a line 49 to an acid settler 60 where the acid is removed from the light ends and hydrocarbons. The output from the acid settler 60 goes to alkylate accumulator 47 which separates alkylate from excess isobutane. The alkylate is passed by a line 50, to a caustic wash (not shown) and then to an alkylate accumulation tank (not shown). The excess isobutane is fed back by a line 48 into the reactor 41. The acid settler 60 settles the acid, and the accumulated acid is pumped back to the reactor 41 through pump 56.

The system includes a source of 100% anhydrous HF which is fed through a pump 51 and control valve 52. A 3-way valve 53 provides switching between feeding the HF to the acid settler 60 or to wash the cell 54. An HF washing of the cell once a day is adequate to minimize build up of a coating on the optical elements. Thus, cleaning would be a daily maintenance operation.

The acid settler 60 has a feed of water to control the water level through a pump 55 and control valve 68. There is also provided a source of sulfolane which is fed through a pump 75 and a control valve 71 into the acid settler 60. Basically the acid settler 70 is a unit for mixing all of the components of the catalyst in a proper mixture, and the output of the acid settler goes through the pump 56 and the on-line analyzer 54 to analyze the catalyst composition and send out appropriate control signals to various valves to automatically adjust the composition of the catalyst and maintain it at optimum level.

FIG. 5 also shows an HF catalyst regeneration section in accordance with the present invention. Part of the output of a pump 56 is fed into an acid stripper 58 through a valve 57. The acid stripper 58 removes the HF from the ASO, sulfolane and water. The removed HF is pumped back to the acid settler 60 by a pump 61 and a valve 62. The bottoms of the acid stripper 58, which is mainly sulfolane, ASO and some water, is passed through a control valve 63 into a sulfolane/ASO separator 64. Since ASO has a density less than sulfolane, ASO is removed from the top of the separator 64 and passed by a line 65 to an ASO disposal. The bottoms of the ASO/sulfolane separator 64, which is mainly sulfolane, is fed back through a pump 66 and a control valve 67 into the mixing area 68 of the acid settler 60.

The signals from the analyzer which control the catalyst composition are the signal for water adjustment which regulates a control valve 68 to control the water level introduced into the acid settler 60 from a source of water. The HF signal from the analyzer controls valves 69, 70 which control the amount or level of HF in the acid settler 60. The valve 69 controls HF flow through a pump 71 from a source of 100% HF acid, and the valve 70 controls flow from the stripper 58. Signals from the analyzer 54 control sulfolane flow to the settler 60 through a valve 71 from a sulfolane source, and through the valve 67 from the separator 64. Analyzer ASO control signals adjust the ASO control valve 57 to regulate the amount of ASO.

The three components, HF, sulfolane and water basically are absorbed the same area of the infrared. One inventive aspect of the present invention is that peak heights or peak areas are not measured independently. Distortions of the main peak which is mostly due to HF are measured. The HF absorbs in the 3500–3600 wave number area in the infrared, as well as water and sulfolane. Water broadens the peak shape of the HF and thus essentially distorts the absorption shape of the HF in the spectrum. This distortion includes a polymer area downfield in the 2400 wave number region where HF/water combinations are found. Sulfolane also distorts the HF peak, and the invention provides for evaluating the distortions of the HF peak to determine the content of water and sulfolane.

Basically the changes in the HF peak are determined by the data processing scheme which is the PLS or PCR. The PLS or PCR reduces the dimensionality of the signal and finds the differences or changes that occur so the comparison to the standards are simplified by this mathematical operation. Through the PLS and PCR the distortions in the peak are readily detected and are calculated by multiplying the spectrum through the vectors that developed by the model.

Figure 6:
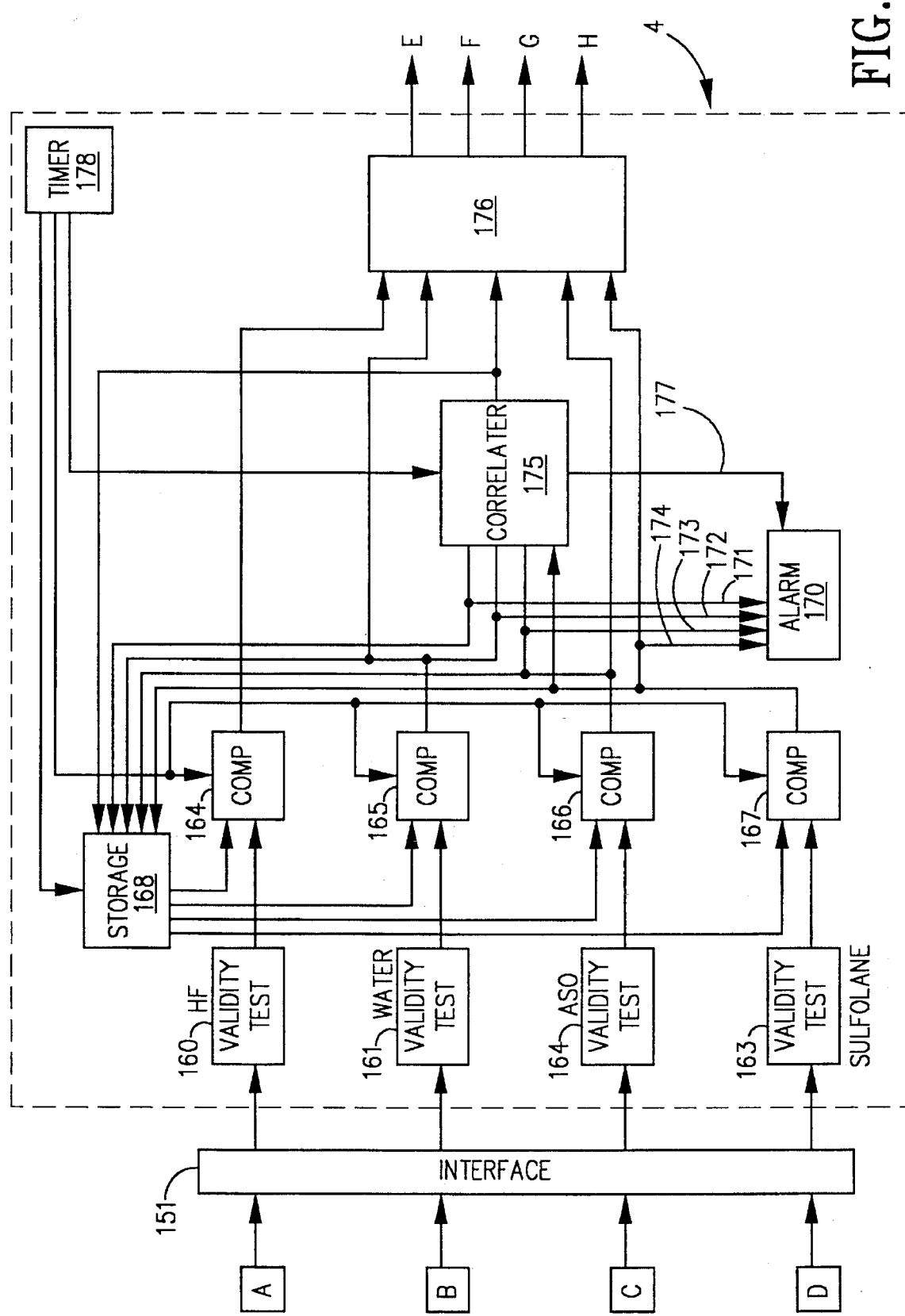
FIG. 6 is another embodiment of the invention for controlling an HF alkylation unit.

With reference to FIG. 6, there is shown a schematic flow diagram of an embodiment of a computer 150 for controlling the HF alkylation unit of FIG. 1. The computer 150 receives data signals representing IR values for at least one, and preferably all, of HF, water, ASO and sulfolane in each monitored stream, for example at any number of point A, B, C and D. For example the FIG. 5 embodiment monitored the feed to the reactor. The computer 150 compares the received data and the results of analysis of the data against limits, reference values and trends, and generates control signals to correct any variation or drift from desired values. If a dangerous condition exists, the computer provides an alarm signal. Normally, alarm signals would be generated only if an emergency condition exists.

The IR data signals representative of HF, water, ASO and sulfolane from the sampling points are fed to the computer 150 via an interface 151. The interface 151 supplies digital signals to data validity test routines 60,61,62,63 located in the computer 150. The test routines 60–63 check the validity of the data relating to the HF, water, ASO and sulfolane of the monitored stream by confirming the data format and/or the nature of the data itself to determine whether or not valid data is being supplied by the interface 151. The outputs from the data validity test routines 60–63 are each coupled to a respective comparator 64–67, wherein the data is compared with limit, and trend reference valves to determine if an abnormal condition exists. The data is also compared with previous data on samples taken from the same monitoring or sampling point to determine if any trends are developing. The limit, trend and reference values are maintained in a storage component 68, and are fed to the comparators 64–67. If an abnormal trend or condition is detected by any one of the comparators 64–67 which indicates a dangerous condition in the process or at the location where the sample was extracted, an alarm signal is fed to an emergency condition alarm 70 via lines 71–74, respectively.

The outputs of the comparators 64–67 are fed to the storage component 68 wherein the results of the analysis are stored with the results of previous samples from the same location. The outputs of comparators 64–67 are also fed to a correlator 75 which compares various combinations of the results of the comparisons performed in the comparators 64–67 with trend and reference information stored in the storage component 68. The correlator 75 provides the results of the correlation of data to a coder 76. The correlator 75 also determines if any trends are developing and if any combination of conditions existing in the engine indicate a dangerous condition. If a dangerous trend or condition is detected, the correlator 75 provides an output signal to the emergency condition alarm 70 via a line 77, and the alarm 70 generates an alarm signal to alert the system operator of the dangerous condition.

Alternatively, the validity routines 60–63 may be replaced with one routine, and the comparators 64–67 could be replaced with a single comparator. The information from each signal generator 7-10 can then be sequentially fed through a single high speed circuit.

The outputs of the correlator 75 and the output of the comparators 64–67 are sent to a coding routine 76 wherein the outputs of the correlator 75 and comparators 64–67 are coded into control codes and other quantities relating to HF, water, ASO and/or sulfolane. The output of the coder 76 sends control signals to various locations of the process of FIG. 5 to correct undesired trends and values, for example to control valves E, F, G and H, e.g. values 68, 69, 70, 71 and 57 of FIG. 5. The operation of the computer 150 may be under control of a timing device 78 which controls the transfer of information between the various portions thereof. The validity test routines 60–63 may include comparison devices to check whether or not the input data falls within a predetermined range or ranges, and circuitry to determine whether the format of the data itself (that is, whether the data word supplied by the interface 151 is of the right length, includes proper codes, etc.). The comparator circuits 64–67 include routines to compare data from the validity test routines 60–63 with reference, trend and limit data stored in the storage component 68. The comparators 64–67 also include circuitry for detecting emergency conditions. The emergency detecting circuits within the comparators 63–65 may comprise a decoding circuit, such as a matrix which is responsive to predetermined data configurations indicative of emergency conditions.

The correlator 75 includes comparison circuits for comparing various combinations of inputs from the comparators 64–67 with reference trend and limit data from the storage component 68. The correlator 75 also may include a decoding circuit for detecting predetermined data configurations which indicate emergency conditions and for feeding an appropriate signal to the alarm 70. The coder 76 receives input information relating to the monitored variables HF, water, ASO and/or sulfolane, and combines such information. The coder 76 detects the existence of various conditions and of various predetermined combinations of conditions, and provides coded data control signals which are fed to the controlled HF alkylation process of FIG. 5. The coder 76 may include a matrix type of coder which provides various output signals in response to predetermined individual input signals and to predetermined combinations of input signals.

While the invention has been described in conjunction with specific embodiments thereof, it is evident that many alternatives, modifications, and variations will be apparent to those skilled in the art in light of the foregoing description. Accordingly, it is intended to embrace all such alternatives, modification, and variations as fall within the spirit and broad scope of the appended claims.

APPENDIX

MHF - Continuous Refinery Acid Prediction Program for Lab-Calc
```
'There MUST be the following files, subdirectories, and directories
'C:\LC\7SEP6445.CAL       spectral calibration file used in prediction
'C:\HF\RESULTS.DAT        file where all of run results of runs are stored
'C:\HF\ERROR.DAT          file where all of errors are stored
'C:\LC\BLANK.SPC          clean empty sample cell spectrum obtained at t=0
'C:\LC\FIP.SPC            regression vector and wavelength region
'C:\LC\WATER.SPC          water correction spectrum 'Initilize MHF , BOMEM, and I/O cabinet
100   free
      noshow : noshow : noshow : noshow : noshow : noshow
      if getleft() < 3000 then xflip
      loadspc "C:\LC\BLANK.SPC"   '#5 #6 blank
      loadspc "C:\LC\FIP.SPC"     '#4 #5
      loadspc "C:\LC\WATER.SPC"   '#3 #4
      #3=-log(#3)
      factor=#2[.]#3
      #3=#3-(#1*factor)
      loadspc "C:\LC\REF.SPC"     '#2 #3 old ref
      #1=-log(#1)
      factor=#3[.]#1
      #1=#1-(#2*factor)
      np=npts(#S)
      for I = 0 to np
            #S(#I) = 10 ^ neg(#S(#I))
      next
      setleft 4050,2453
      portout 905, 0           'clear RTI-820 flags
      portout 908, 4           'set RTI-820 DIO port1 in port2 out
      portout 911, 0           'turn off all relays
      colput 102, 1            'set up for aquisition autosave
      dim directory(12)
      string $directory = "C:\HF"   'define default .SPC directory
      string $directory, -8         'set up the default .SPC directory
      dos "RL4ON" : dos "RL4OFF"

'Start the continuous loop here
500   free : pauseoff : printhue 7,0,0   'print white on black
      dim tempText(12),fileName(12),errlog(12)
      portout -30, 2           'tab value
      gosub 16000              'watchdog timer reset subroutine
      gosub 13500              'digital input subroutine
      if alarm = 1 then 510 else 520   'If pressure in secondary barrier
510   gosub 14000 : gosub 14050 : gosub 53500 'log error and output 4 mA
      delay = 60 : gosub 15900   '1 hour delay before next attempt
      portout 911, 0 : goto 100  'bypass sample cell
520   free numb,button,acid,alarm
      gosub 13750
      portout 911, 2           'dos "RL2ON" 'flow through the sample cell
      print " Opening acid valves to sample cell "
      seconds =10 : gosub 15950     's delay for valves to open
      gosub 13500              'digital input subroutine
      if acid = 1 then 900     'if valves are open goto 900
      gosub 14000 : gosub 14100 : gosub 53500 'log error and output 4 mA
```

```
                delay = 30 : gosub 15900        '30 min delay before next attempt
                goto 100
        900     free button,acid,alarm,numb
                channel = 11 : slope = 0.0001955 : inter = 0.80   'spcgrav .000733
                gosub 16500 : gra = (rnd(value*10000))/10000 'specific gravity
                print " Acid valves are open to sample cell "
                channel = 10 : slope = 1.1085 : inter = -1.1085 'point to acid flow ch
                gosub 16500 : flowrate = rnd(value/gra)   'record acid flow rate
                if flowrate < 50 or flowrate > 1500 then gosub 14000 : gosub 14400
                goto 1000
                if flowrate > 20 then 1000      'If flowrate < 15 then abort
                gosub 14000 : gosub 14150 : gosub 53500
                delay = 10 : gosub 15900 : goto 100
'*********************************************************************
'Time to stop the acid flow and allow temperature control
        1000    gosub 16000                     'watchdog timer reset subroutine
                gosub 13750
                seconds = 5 : gosub 15950 : minute = clock(-3)
                print "Acid is flowing. Wait for 0, 15, 30, 45 min. Now it is ";minute
                if minute = 0 then goto 1050    'time to close the acid return valve
                if minute = 15 then goto 1050   'and allow temperature control
                if minute = 30 then goto 1050
                if minute = 45 then goto 1050 else goto 1000
        1050    portout 911, 0                  'dos "RL2OFF" 'bypass the sample cell
                print " Bypassing sample cell "
                seconds = 10 : gosub 15950
                day   = clock(-5)               'and allow temperature control
                hour  = clock(-4)
                v = (day * 10000) + (hour * 100) + minute
                string $tempText, -19
                string $tempText(0) = "0"
                if day < 10 then string $fileName = $tempText(0, 5)
                if day >= 10 then string $fileName = $tempText(1, 6)
                gosub 13500                     'digital input subroutine
                if acid = 1 then 1090 else 1095
        1090    gosub 14000 : gosub 14200 : gosub 53500
                goto 100
        1095    free button,acid,alarm,numb
        1100    gosub 16000                     'watchdog timer reset subroutine
                gosub 13750
                seconds = 5 : gosub 15950 : minute = clock(-3)
                print "Sample cell bypassed. Wait for 5, 20, 35, 50 min. Now it is ";minute
                if minute = 5 then 1105         'time to start data acquisition
                if minute = 20 then 1105
                if minute = 35 then 1105
                if minute = 50 then 1105 else 1100
'*********************************************************************
'Acquire refrence spectrum
        1105    gosub 13750
                portout 911, 4                  'dos "RL3ON" 'place mirror in reference position
                print " Move mirrors in the reference cell position "
                seconds = 5 : gosub 15950       'time delay for mirror motion
                free alarm,acid,button,numb
                string $fileName(6, 7), "R"
                colput 300, 64                  'number of reference scans
                colput 202, $fileName           'put filename for autosave
```

```
            colput 100, 255            'set up aquisition
            print $fileName:" Acquiring reference spectrum "
            gosub 13750
            gosub 16000                'reset wtchdog timer
            colstart                   'start auiring reference spectrum
    1110    colget 100, status : if status <> 0 then 1110
            loadspc $fileName          '#1 #2 new ref
            gosub 15000 : setcolor 3   'screen display subroutine
            seconds = 2 : gosub 15950  'time delay for mirror motion
            #1=-log(#1)
            factor=#4[.]#1
            #1=#1-(#3*factor)
            np=npts(#S)
            for I = 0 to np
                    #S(#I) = 10 ^ neg(#S(#I))
            next
            free factor,np
            gosub 15000 : setcolor 2
            #1=#1/#2
'***********************************************************************
'Acquire sample spectrum
            gosub 16000                'watchdog timer reset subroutine
            portout 911, 0     'doe "RL3OFF" 'place mirror in sample position
            print " Move mirrors to the sample cell position "
            seconds = 5 : gosub 15950  's delay for mirror motion
            channel = 8 : slope = 0.08798 : inter = 31.912
            gosub 16500 : rtemprt = (rnd(value*10))/10 'ambient temperature
            channel = 12 : slope = 0.08798 : inter = 31.912
            gosub 16500 : hutmp = (rnd(value*10))/10 'sample cell temp
            channel = 9 : slope = 0.08798 : inter = 31.912
            gosub 16500 : ctemprt = (rnd(value*10))/10 'sample cell temp
            if ctemprt < 78 and ctemprt > 68 then 1115
            gosub 14000 : gosub 14300 : gosub 53500 : goto 100
    1115    string $fileName(6, 7), "S"    'end filename with S
            print " Acquiring sample spectrum ";$fileName
            colput 300, 76             'number of sample scans
            colput 202, $fileName      'put filename for autosave
            colput 100, 255            'set up aquisition
            gosub 13750
            gosub 16000                'watchdog timer reset subroutine
            colstart                   'start aquiring sample spectrum
    1120    colget 100, status : if status <> 0 then goto 1120
            loadspc $filename          'load Sn as #1
            gosub 15000 : setcolor 3   'screen display subroutine
            gosub 12500                'check for low throughput
            seconds = 2 : gosub 15950
'***********************************************************************
(Eq. 1) 'Calculate absorbance, treat, and output data
            gosub 16000                'reset watchdog timer
            #1=#1/#2
            #1=-log(#1)
            factor=#5[.]#1
            #1=#1-(#4*factor)
            #1=#1-#6
            free factor,alarm,acid,seconds,slope,inter,channel,day,hour,minute
            gosub 15000 : setcolor 1   'display subroutine
```

(Eq. 2)
```
             seconds = 2 : gosub 15950
             gosub 17000                    'Do 13 point 1st-order derivative
             gosub 15000 : setcolor 4
             seconds = 2 : gosub 15950
             s=30 : lx=3949.4 : rx=3023.5 : gosub 14500 '900 ld SG smooth
             gosub 18000                    'Do limited normalization
             gosub 15000 : setcolor 2       'display subroutine
             seconds = 2 : gosub 15950      'time delay
             gosub 12000                    'check for HF vapor in sec barr.
             open "O",#1,"C:\LC\9NOV3353.CAL"
             gosub 18000                    'PLS-1 prediction and output
             HF  = Yn(0)   : HFR = resid(0)
             SUL = Yn(2)   : ASO = Yn(3)
             SULR = resid(2) : ASOR = resid(3)
             WAT = Yn(1)   : WATR = resid(1)

noshow : noshow
             free Yn,resid

HF =HF  * 0.92  : HFR=rnd(HFR*100000)/1000  : HF =rnd(HF *100)/100
             WAT=WAT * 0.92  : WATR=rnd(WATR*10000)/1000 : WAT=rnd(WAT*1000)/1000
             SUL=SUL * 0.92  : SULR=rnd(SULR*100000)/1000 : SUL=rnd(SUL*100)/100
             ASO=ASO * 0.92  : ASOR=rnd(ASOR*100000)/1000 : ASO=rnd(ASO*100)/100
             TOTALL=HF+WAT+SUL+ASO : TOTALL=rnd(TOTALL*100)/100 gosub 13500                    'digital input subroutine
             if button = 1 then 1130 else 1150
       1130  portout 911, 3 : seconds=1 : gosub 15950
             portout 911, 2 'dos "RL1RST
             string $fileName(6, 8), "B#"   'end filename with B for button
       1150  free button,acid,alarm,numb open "O", #2, "RESULTS.DAT"
             seek #2, -0
             print #2, $fileName;",";hutmp;",";rtemprt;",";ctemprt;",";
             print #2, flowrate;",";gra;",";
             print #2, HF;",";WAT;",";SUL;",";ASO;",";HFR;",";WATR;",";SULR;",";ASOR
             close #2 printline 22
             if HFR < 0.7 then printhue 1,0,0 else printhue 3,0,0
             print "HF=";HF,"Water=";WAT,"Sulfolane=";SUL,"ASO=";ASO;
             print " ST=";ctemprt,"RT=";rtemprt,"HT=";hutmp
             print "HF er=";HFR,"Wat er=";WATR,"Sul er=";SULR;
             print " ASO er=";ASOR,"FR=";flowrate,"SG=";gra
             print "File name=";$fileName,"Total=";TOTALL
             printhue 7,0,0                 'print white on black lprint $errlog;" Log (MMDDHHMM) "," Filename = ";$fileName
             lprint " Cell T=";ctemprt;"F Ref T=";rtemprt;"F Hut T=";hutmp;
             lprint "F Flow R=";flowrate;"cc/min Spc G=";gra;"g/cc "
             lprint " HF    =";HF," ","% Res=";HFR
             lprint " Water  =";WAT," ","% Res=";WATR
             lprint " Sulfolane=";SUL," ","% Res=";SULR
             lprint " ASO    =";ASO," ","% Res=";ASOR
             lprint " Total  =";TOTALL
```

```
            lprint " "

gosub 13750
            portout 911, 2         'dos "RL2ON" 'turn on acid flow valve ASAP
            print "--acid valves are open to the cell--"
            seconds = 1 : gosub 15950      '1 seconds delay before 4-20 mA 'HF 4-20 mA channel output
      1160  channel = 0 : slope = 76.62  : inter = -3567
            if HF > 100   then HF = 100
            if HF < 50    then gosub 54000 : goto 1162
            If HFR > 0.5  then gosub 54000 : goto 1162
            value = HF : gosub 53000
            seconds = 1 : gosub 15950      '1 seconds delay before 4-20 mA
            print "finished HF channel"

'Water 4-20 mA channel output
      1162  channel = 1 : slope = 255.41  : Inter = 263.846
            if WAT < 0    then WAT = 0
            If WAT > 15   then gosub 54000 : goto 1164
            If WATR > 0.5 then gosub 54000 : goto 1164
            value = WAT : gosub 53000
            seconds = 1 : gosub 15950      '1 seconds delay before 4-20 mA
            print "finished water channel"

'Sulfolane 4-20 mA channel output
      1164  channel = 2 : slope = 76.617 : inter = 264.205
            If SUL < 0    then SUL = 0
            if SUL > 50   then gosub 54000 : goto 1166
            if SULR > 0.5 then gosub 54000 : goto 1166
            value = SUL : gosub 53000
            seconds = 1 : gosub 15950      '1 seconds delay before 4-20 mA
            print "finished sulfolane channel"

'ASO 4-20 mA channel output
      1166  channel = 4 : slope = 255.349 : Inter = 264.635
            If ASO < 0    then ASO = 0
            if ASO > 15   then gosub 54000 : goto 1168
            if ASOR > 0.5 then gosub 54000 : goto 1168
            value = ASO : gosub 53000
            seconds = 1 : gosub 15950      '1 seconds delay before 4-20 mA
            print "finished ASO channel"
            seconds = 1 : gosub 15950      '1 seconds delay before 4-20 mA 1168  free HF,HFR,WAT,WATR,SUL,SULR,ASO,ASOR,TOTALL day    = clock(-5)
            hour   = clock(-4)
            minute = clock(-3)
            pakName = (hour * 100) + minute
            If pakName > 2355 and pakName < 2358 then goto 1180 'pak at midnight
            delay = 1 : gosub 15900 : goto 1185
            goto 500               'restart the cycle
      1180  dos "COPY C:\NOLANTAS.BAT C:\AUTOEXEC.BAT"
      1185  portout 850, 1 : portout 850, 1
```

END

```
'Check for HF vapor in secondary barrier and log detection
12000  trsh = abs(#S(#18)-((#S(#16)+#S(#20))/2))
       if trsh < .0007 then free trsh : RETURN
       gosub 14000              'obtain errlog date & time
       open "O", #3, "ERROR.DAT"
       seek #3, -0
       print #3, $errlog, "HF vapor detected in the secondary barrier"
       close #3
       printhue 3,0,0
       print "***** HF vapor detected in secondary barrier *****"
       printhue 7,0,0
       lprint $errlog, " HF vapor detected in secondary barrier"
       lprint " "
       free trsh
  RETURN
```

```
'Check for extrusion of "O" ring
12500  maximum = max(#s)
       if maximum > 1.8 then free maximum : RETURN
       gosub 14000              'obtain errlog date & time
       open "O", #3, "ERROR.DAT"
       seek #3, -0
       print #3, $errlog, "*** Sample cell IR throughput is too low ***"
       close #3
       printhue 3,0,0
       print " * Sample cell IR throughput is too low **"
       printhue 7,0,0
       lprint $errlog, " Sample cell IR throughput is too low"
       lprint " "
  RETURN
```

```
'Digital input and signal sorting subroutine
13500  gosub 16000              'reset watch-dog timer
       portin 910, numb         'read port-1
       button = int(((numb / 2) - int(numb / 2)) * 2)
       acid   = int(((numb / 4) - int(numb / 4)) * 2)
       alarm  = int(((numb / 8) - int(numb / 8)) * 2)
  RETURN
```

```
'Do cell flush with HF
13750  gosub 16000              'reset watch-dog timer
       portin 910, numb         'read port-1
       flush = int(((numb /16) - int(numb /16)) * 2)
       if flush = 1 then 13755
       free numb,flush
  RETURN
13755  portout 911, 0           'does "RL2OFF" 'bypass sample cell
       gosub 53500              'output data not valid
       gosub 11000
```

```
           print "flushing the sample cell with 100% HF"
           open "O", #3, "ERROR.DAT"
           seek #3, -0
           print #3, $errlog,"Start of sample flush with 100% HF"
           close #3
           lprint $errlog,"Start of sample flush with 100% HF"
           lprint " "
           portout 911, 4       'dos "RL3ON" 'place mirror in reference pos.
           seconds = 5 : gosub 15950       'time delay for mirror motion
           colput 300, 64                'number of reference scans
           colput 202, $errlog           'put filename for autosave
           colput 100, 255               'set up aquisition
           gosub 16000                   'watch-dog timer reset subroutine
           colstart                      'start auiring reference spectrum
13756      colget 100, status : if status <> 0 then 13756
           portout 911, 0       'dos "RL3OFF" 'place mirror in reference pos.
           seconds = 5 : gosub 15950       'time delay for mirror motion
           gosub 14000
           colput 300, 64                'number of reference scans
           colput 202, $errlog           'put filename for autosave
           colput 100, 255               'set up aquisition
           gosub 16000                   'watch-dog timer reset subroutine
           colstart                      'start auiring reference spectrum
13757      colget 100, status : if status <> 0 then 13757
13800      gosub 16000
           noshow
           colput 300, 1                 'number of reference scans
           colput 202, "TEST"            'put filename for autosave
           colput 100, 255               'set up aquisition
           colstart                      'start auiring reference spectrum
13801      colget 100, status : if status <> 0 then 13801
           loadspc "TEST"
           gosub 15000
           portin 910, numb              'read port-1
           flush = int(((numb /16) - int(numb /16)) * 2)
           if flush = 1 then 13800
           print "flushing is over. Wating 10 min. for MHF catalyst circulation"
           portout 911, 2       'dos "RL2ON" 'flow through sample cell
           gosub 14000
           open "O", #3, "ERROR.DAT"
           seek #3, -0
           print #3, $errlog,"End of cell flush with 100% HF"
           close #3
           lprint $errlog,"End of cell flush with 100%"
           lprint " "
           gosub 16000
           delay = 1 : gosub 15900    '10 minutes delay before next attempt
           goto 1185

'***********************************************************************
'***********************************************************************
'Obtain the proper date and time for error logs subroutine
14000      month  = clock(-6)
           day    = clock(-5)
           hour   = clock(-4)
           minute = clock(-3)
```

```
            v = (month * 1000000) + (day * 10000) + (hour * 100) + minute
            string $tempText, -19
            string $tempText(0) = "0"
            if month < 10 then string $errlog = $tempText(0, 7)
            if month >= 10 then string $errlog = $tempText(1, 8)
            free month,day,hour,minute
      RETURN
'****************************************************************
'****************************************************************
'Log acid valve not open to sample cell error subroutine
14100 open "O", #3, "ERROR.DAT"
            seek #3, -0
            print #3, $errlog, "Acid valve is not open to the sample cell"
            close #3
            printhue 3,0,0
            print " Acid valve is not opening to the sample cell. Waiting 10 min"
            printhue 7,0,0
            lprint $errlog, "Acid valve is not open to sample cell"
            lprint " "
      RETURN
'****************************************************************
'****************************************************************
'Log high pressure alarm in the secondary barrier, possible HF leak
14050 open "O", #3, "ERROR.DAT"
            seek #3, -0
      print #3, $errlog, "High pressure alarm in the sec. barrier pos. HF leak"
            close #3
            printhue 3,0,0
print "High pressure alarm in the secondary barrier pos. HF leak. Waiting 10min"
            printhue 7,0,0
            lprint $errlog, "High pressure alarm in secondary barrier HF leak ?"
            lprint " "
      RETURN
'****************************************************************
'****************************************************************
'Log acid not flowing through the cell error subroutine
14150 open "O", #3, "ERROR.DAT"
            seek #3, -0
      print #3, $errlog, "Acid valve is open, but there is no flow through cell"
            close #3
            printhue 3,0,0
print "Acid valve is open, but there is no flow through the cell. Waiting 10min"
            printhue 7,0,0
            lprint $errlog, "Acid valve is open, but there is no flow through cell"
            lprint " "
      RETURN
'****************************************************************
'****************************************************************
'Log acid not bypassing cell error subroutine
14200 open "O", #3, "ERROR.DAT"
            seek #3, -0
            print #3, $errlog, "Acid is not bypassing the sample cell"
            close #3
            printhue 3,0,0
            print "*****Acid is not bypassing the sample cell*****"
            printhue 7,0,0
```

```
       lprint $errlog, "Acid is not bypassing the sample cell"
       lprint " "
 RETURN
'**************************************************************
'**************************************************************
'Log acid cell temperature exceeds the limits subroutine
14300  open "O", #3, "ERROR.DAT"
       seek #3, -0
       print #3, $errlog, ctemprt; "F. Sample cell temperature is out of limits"
       close #3
       printhue 3,0,0
       print ctemprt; "F. Sample cell temperature is out of range"
       printhue 7,0,0
       lprint $errlog, ctemprt; "F. Sample cell temperature is out of limits"
       lprint " "
 RETURN
'**************************************************************
'**************************************************************
'Acid flow rate out of range error documentation subroutine
14400  open "O", #3, "ERROR.DAT"
       seek #3, -0
       print #3, $errlog, flowrate;"cc/min. Acid flow rate is out of limits"
       close #3
       printhue 3,0,0
       print flowrate; "cc/min. Acid flow rate is out of range"
       printhue 7,0,0
       lprint $errlog, flowrate; "cc/min. Acid flow rate is out of limits"
       lprint " "
 RETURN
'**************************************************************
'**************************************************************
'S-G smooth of 60 points
14500  zsn = 2
       deg = 2
       d  = 0
       m=(s-1)/2
       dim Ps(s) : fillbeg -m : fillinc 1 : Ps=fill(Ps)
       dim X(deg,s) : X=1
       for i=1 to deg-1
         for j=1 to i
           X(i)=X(i)*Ps
         next j
       next i
       dim Z(deg,deg) : Z = X [#] trans(X) : invertdp Z
       dim T(deg,s) : T = Z [#] X : free Z,X
       Ps=T(d)                    'get row for conviv
       reverse Ps                 'flip it around for convolve
       slot=getsfile()+1
       newspc atmp(npts(#s))
       atmp=#slot
       convolve #s,Ps
       if getffp()>getflp() and lx>getffp() then lx=getffp() 'Put smoothed and
       if getffp()<getflp() and lx<getffp() then lx=getffp() 'unsmoothed regns
       dim atmp(npts(#s(lx,rx)))                              'back together.
       atmp=#s(lx,rx)
       #slot(lx,rx)=atmp
```

```
            noshow
            free fac,deg,d,s,m,Ps,X,Z,T,Ix,rx,atmp
      RETURN
'*********************************************************************
'*********************************************************************

'Screen display subroutine
15000   blankbox : autoscale : display
      RETURN
'*********************************************************************
'*********************************************************************

'Time delay subroutine (delay in minutes)
15900   for i = 0 to delay
            gosub 16000 : timer = clock(0)
15910   if not(clock(62)) then 15910
        next
      RETURN
'*********************************************************************
'*********************************************************************

'Time delay subroutine (delay in seconds)
15950   timer = clock(0)
15960   if not(clock(seconds)) then 15960
      RETURN
'*********************************************************************
'*********************************************************************

'Clock reset subroutine
16000   portout 850, 255 : portout 850, 255
      RETURN
'*********************************************************************
'*********************************************************************

'Analog 4-20 mA input subroutine (channel, slope, inter, => value)
16500   portout 905, 0              'clear flags
        portout 897, channel        'point to appropriate channel
        portout 898, 0              'convert command
        for I = 0 to 1000 : next    'time for data to settle
        portin 899, lowbyte         'read lowbyte (8 bits)
        portin 900, highbyte        'read highbyte (4 bits)
        highbyte = ((highbyte / 8.0) - (int(highbyte / 8.0))) * 8.0
        number = highbyte *256 + lowbyte  'convert to number (1 to 2047)
        if number > 2047 then number = 2047
        if number < 1   then number = 1
        value = slope * number + inter    'convert to appropriate value
      RETURN
'*********************************************************************
'*********************************************************************

'13 point quartic 1st-order derivative convolution subroutine
17000   s = (2*int(13/2))+1
        deg = 5 : d = 1
        m=(s-1)/2
        dim Ps(s) : fillbeg -m : fillinc 1 : Ps=fill(Ps)
        dim X(deg,s) : X=1
        for I=1 to deg-1
          for j=1 to i
            X(i)=X(i)*Ps
          next j
        next i
        dim Z(deg,deg) : Z = X [*] trans(X) : invertdp Z
```

```
        dim T(deg,s) : T = Z [#] X : free Z,X
        Ps=T(d)                  'get row for conviv
        reverse Ps               'flip it around for convolve
        convolve #S,Ps
        free s,deg,d,m,Ps,X,Z,T
    RETURN
'**************************************************************
'**************************************************************

'Hydrocarbon zapping subroutine (draw streight line between 3050 to 2800)
17500  le=index(#s(lle))
       re=index(#s(rre))
       np=npts(#s)
       dim temp(np)
       temp=#s
       npr=abs(le-re)
       fillbeg temp(le)
       fillinc (temp(re)-temp(le))/npr
       temp(le,re)=fill(temp(le,re))
       #s=temp
       free le,re,np,temp,npr,lle,rre
    RETURN
'**************************************************************
'**************************************************************

'Normalize one wide regeion subroutine
18000  regsum = 0
       le=index(#s(3949.4))
       re=index(#s(2452.6))
       for i=le to re
           regsum=regsum+abs(#s(#i))
       next
       for i=le to re
           #s(#i)=#s(#i)/regsum
       next
       free le,re,regsum
    RETURN
'**************************************************************
'**************************************************************

'Normalize two regeions subroutine
18500  regsum = 0
       le=index(#s(3949.4))
       re=index(#s(3023.5))
       for i=le to re
           regsum=regsum+abs(#s(#i))
       next
       le=index(#s(2819.1))
       re=index(#s(2452.6))
       for i=le to re
           regsum=regsum+abs(#s(#i))
       next
       le=index(#s(3949.4))
       for i=le to re
           #s(#i)=#s(#i)/regsum
       next
       free le,re,regsum
    RETURN
'**************************************************************
```

```
'''''''''''''''''''''''''''''''''''''''''''''''''''''''''''''''''''''''''''''''''
'PLS-Prediction subroutine
19000  free flags
       dim flags(60)              'to hold all parameter flags
       flags=0 : m=0 : n=0 : a=0 : p=0
       flags(4)=1 : flags(0)=1 : flags(16)=1
       free W,Bx,By,Vr,vt,mode,bands,L,F,lambda,Yn,Xn,B,Xt,nt
       free dev,cname,Mx,My,Sdx,Sdy,fs,fcnt,resid,fres,prob,fstat,stat,Ypm,C
       read #1, l,m,p,flags       'header same for all files
       dim bands(flags(1),4),cname(m,15)   'dim for regions and components
       dim Yn(m),Xn(p),Xt(2,p)    'dim for prediction
       dim stat(3,m),Ypm(m)       'arrays for stats for CFL pred.
       read #1, bands,cname       'get band parms and components
       if ((bands(0,0)-bands(0,1))>0)<>((getleft()-getright())>0) then xflip
       If flags(9)<2.1 goto 19105 'V2.1 or higher?
         n=flags(10)
         dim C(4)
         C(0)=0.196854 : C(1)=0.115194 : C(2)=0.000344 : C(3)=0.019527
'PLS-1
19105  vt = sum(flags(20,20+m-1)) : vy=0 : mc=0
       dim W(vt,p),Bx(vt,p),Vr(vt),resid(m)
       If flags(9)>=2.1 then dim fres(m),fstat(m),prob(m)  'V2.1 or higher?
       for i=0 to m-1
         dim Wt(flags(20+i),p),Bxt(flags(20+i),p),Vrt(flags(20+i))
         onerror 19130
         read #1, Wt,Bxt,Vrt
         onerror -1
         for j=0 to flags(20+i)-1
           W(j+vy)=Wt(j)
           Bx(j+vy)=Bxt(j)
         next j
         Vr(vy,vy+flags(20+i)-1)=Vrt
         vy=vy+flags(20+i)
         free Wt,Bxt,Vrt
         If flags(9)<2.1 goto 19110       'V2.1 or higher?
           onerror 19130
           read #1,Frt
           fres(i)=Frt
           free Frt
           onerror -1
19110  next i
       if mc=-99 goto 1020
       If flags(4)<>1 goto 19115
         dim Mx(p),My(m)
         onerror 19130
         read #1, Mx,My
         onerror -1
19115  If flags(3)<>1 goto 19120
         dim Sdx(p),Sdy(m)
         onerror 19130
         read #1, Sdx,Sdy
         onerror -1
19120  If (flags(4)=1) or (flags(5)=0) then close #1 : goto 20000
         dim Mx(p)
         onerror 19130
         read #1, Mx
```

```
          onerror -1
          close #1
          goto 20000
19130    i=m-1 : mc=-99:free vt,W,vy,Bx,Vr,Bxt,Wt,Vrt,Mx,My,Sdx,Sdy,fres
          goto 19110

'*******************************************************************

'Predict the sample in the #s slot
20000    gosub 52000              'extract Xn bands from #s spectrum
20300    gosub 21000              'do the proper predict method
          return

'*******************************************************************

'PLS-1 predict
21000    Yn=0
          dim Xs(p) : Xs=Xn        'holds the raw processed spectrum
          vt=0
          for i=0 to m-1           'rotate through the components
            Xn = Xs : Xt(1)=0      'raw data back in Xn for each component
            for j=0 to flags(20+i)-1    'rotate through the vectors
              Tn = Xn [#] trans(row(W(vt+j)))   'calculate score
              Yn(i) = Yn(i) + (Vr(vt+j) * Tn)   'add contribution to conc.
              Xn = Xn - (Bx(vt+j) * Tn)         'subtract vector from sample
              Xt(1) = Xt(1) + (Bx(vt+j) * Tn)   'reconstruct spectra
            next j                              'next vector
            vt = vt + flags(20+i)
            if flags(3)=1 then Xt(1)=Xt(1)*Sdx
            if flags(4)=1 then Xt(1)=Xt(1)+Mx
            resid(i)=sqrt(sumd2(Xt(0),Xt(1)))
            if flags(9)>=2.1 then gosub 30000   'V2.1 compute Fstat
          next i                                'next component
          if flags(3)=1 then Yn=Yn*Sdy          'Un-variance scale
          if flags(4)=1 then Yn=Yn+My           'Un-Mean center
          if flags(6)=0 goto 21100              'Un-Pathlength correct
          for i=1 to m-1
            Yn(i)=Yn(i)/Yn(0)
          next
21100    free vt,Xs,Tn
          return 'Compute F statistic and probability
30000    IF FLAGS(0)<>1 GOTO 30010
          fstat(i)=squared(resid)*n/fres(i)
          PROB(i)=(FSTAT(i)^(1/3)*(1-2/(9*(N-FLAGS(20+i)-2))))-(1-2/9)
          PROB(i)=PROB(i)/SQRT((FSTAT(i)^(2/3))*2/(9*(N-FLAGS(20+i)-2))+2/9)
          PROB(i)=(PROB(i)*C(0))+((PROB(i)^2)*C(1))+((PROB(i)^3)*C(2))
          prob(i)=prob(i)+((PROB(i)^4)*C(3))+1
          PROB(i)=PROB(i)^(-4) : PROB(i)=NEG(PROB(i))*0.5+1
          RETURN
30010    fstat=squared(resid)*n/fres
          PROB=(FSTAT^(1/3)*(1-2/(9*(N-FLAGS(20)-2))))-(1-2/9)
          PROB=PROB/SQRT((FSTAT^(2/3))*2/(9*(N-FLAGS(20)-2))+2/9)
          PROB=(PROB*C(0))+((PROB^2)*C(1))+((PROB^3)*C(2))+((PROB^4)*C(3))+1
          PROB=PROB^(-4) : PROB=NEG(PROB)*0.5+1
          RETURN

'*******************************************************************
```

'Extract bands from #s spectrum, preprocess and put in Xn

```
52000  for I=0 to flags(1)-1              'rotate through all the bands
         if npts(#s(bands(i,0),bands(i,1)))=bands(i,3) goto 52010
           printhue 8,6,1:printline 24:beep
           print "Spectrum is not the same resolution as training set - ";
           pauseon : print "cannot complete calculation"
           pauseoff
           i=flags(1)-1
         next i : return 52010  if flags(7)=0 goto 52015           'Baseline correct this band?
         dim blx(bands(i,3)),bly(bands(i,3))
         blx=fill(blx):bly=#s(bands(i,0),bands(i,1))
         c1=(sum(bly))*(sum(squared(blx)))-(sum(blx))*(sum(blx*bly))
         c1=c1/(bands(i,3)*(sum(squared(blx)))-(squared(sum(blx))))
         c2=(bands(i,3))*(sum(blx*bly))-(sum(blx))*(sum(bly))
         c2=c2/(bands(i,3)*(sum(squared(blx)))-(squared(sum(blx))))
         bly=bly-(blx*c2+c1)
         #s(bands(i,0),bands(i,1))=bly
         free blx,bly,c1,c2
```

'Calculate number of points used in region and remainder (if not even divisor)
```
52015  div=int(bands(i,3)/bands(i,2))     '# pts used in this band
         mod=bands(i,3)-div*bands(i,2)      'remainder
         if mod<>0 then div=div+1           'remain adds extra point
         dim stor(div,bands(i,2))           'temp matrix for avg or skip
         dim Uc(bands(i,2),1) : Uc=1        'Unit column for avg
         dim Xres(div)                      'resultant corrected band if flags(2)=1 goto 52050           'Average (0) or Skip (1)?
```

'Put data in matrix and calculate data point averages
```
52020  stor = row(#s(bands(i,0),bands(i,1)))  'spectrum in rows of pt spcing
         Xres = stor [*] Uc                 'calc row sums
52030  Xres = Xres/bands(i,2)               'divide by point spacing
         if mod<>0 then Xres(div-1)=(Xres(div-1)*bands(i,2))/mod 'handle last pt
         goto 52100
```

'Put data into matrix and extract the skipped points
```
52050  stor = row(#s(bands(i,0),bands(i,1)))  'spectrum in rows of pt spcing
         transpose stor                     'transpose to rows of div
         Xres = row(stor(0))                'extract pt skipped spectrum 52100  if flags(5)=0 goto 52110             'MSC preprocess this band?
         dim Mreg(div)
         Mreg=Mx(pttot,pttot+div-1)
         c1=(sum(Xres)*sum(squared(Mreg)))-(sum(Mreg)*sum(Mreg*Xres))
         c1=c1/(p*sum(squared(Mreg))-squared(sum(Mreg)))
         c2=(p*(sum(Mreg*Xres)))-(sum(Mreg)*sum(Xres))
         c2=c2/(p*sum(squared(Mreg))-squared(sum(Mreg)))
         Xres=(Xres-c1)/c2
```

'Save in Xn for prediction
```
52110  Xn(pttot,pttot+div-1)=Xres           'add band data to target array
         pttot=pttot+div                    'point total, so far
```

```
            free stor,Xres,Uc,div,mod,Mreg,c1,c2
            next I                      'start next band
            free pttot
            Xt(0)=Xn                    'for resid calc
            if flags(4)=1 then Xn=Xn-Mx    'Mean center the data?
            if flags(3)=1 then Xn=Xn/Sdx   'Variance scale the data?
            return RETURN
    '*************************************************************
    '*************************************************************

'Analog 4-20 mA output subroutine (channel, value, slope, inter)
    53000   number = rnd((slope * value) + inter)  'prepare number from value
            if number > 4095 then number = 4095    'error-check high end
            if number < 1    then number = 0       'error-check low end
            highbyte = int(number/256)             'compose highbyte
            lowbyte  = int((number/256 - highbyte) * 256)  'compose lowbyte
            portout 905, 0
            portout 902, channel           'point to appropriate channel
    53010   portin 903, dacstat : if dacstat <> 4 then 53010
            portout 902, lowbyte
    53020   portin 903, dacstat : if dacstat <> 4 then 53020
            portout 902, highbyte
    RETURN
    '*************************************************************
    '*************************************************************

'Output 4 mA data invalid signal to all channels subroutine
    53500   for i = 0 to 4
            channel = i
            gosub 54000
            next
    RETURN
    '*************************************************************
    '*************************************************************

'Output 4 mA data invalid signal to the appropriate channel (channel)
    54000   seconds = 1 : gosub 15950
            portout 902, channel           'point to appropriate channel
    54010   portin 903, dacstat : if dacstat <> 4 then 54010
            portout 902, 0
    54020   portin 903, dacstat : if dacstat <> 4 then 54020
            portout 902, 0
    RETURN
    '*************************************************************
    '*************************************************************
```

What is claimed is:

1. A method of controlling the composition of an HF acid catalyst in a reactor of an HF alkylation system wherein said HF acid catalyst includes HF, water, ASO and an additive for reducing the vapor pressure of said HF acid catalyst, said method comprising the steps of:
    (a) obtaining a sample from a stream of said HF acid catalyst;
    (b) passing said sample to an analyzer including an attenuated total reflectance cell;
    (c) regulating temperature of said sample to that of a calibration standard temperature;
    (d) generating signals representative of reference and measured spectra for at least said HF, said water and said additive in said sample;
    (e) processing said spectra signals to correct for instrumental variation in accordance with:

$$A_{corr} = \log_{10}\{S_o/S[R_o/R]\};$$

wherein
    $A_{corr}$=corrected sample absorbance spectrum;
    S=current sample single beam spectrum;
    $S_o$=sample single beam spectrum obtained at time 0 with an empty cell;
    R=current reference cell single beam spectrum; and
    $R_o$=reference cell single beam spectrum obtained at time 0
    (f) generating a derivative of said corrected sample absorbance spectrum;
    (g) normalizing said derivative in accordance with;

$$D_{norm} = D_i / \sum_{2100}^{4100} |D_i|;$$

wherein
    $D_{norm}$=normalized derivative spectral element;
    $D_i$=derivative spectral element; and
    4100–2100=spectral region, cm$^{-1}$;
    (h) multiplying stored model vectors by spectral elements of said normalized derivative to obtain values indicative of the amount of said HF, said water and said additive in said sample;
    (i) comparing said values to reference values to obtain differences, and
    (j) controlling the relative amounts of said HF, said water and said additive in said stream of said HF acid catalyst in response to said differences to provide a predetermined HF acid composition in said reactor; and
    wherein steps (d) through (h) are performed on a computer with a computer program.

2. The method of claim 1 wherein said additive is sulfolane.

3. The method of claim 1 wherein steps (a) and (b) are performed automatically.

4. The method of claim 2 wherein in step (i) said values are compared to reference values to obtain difference signals, and wherein in step (j) the relative amounts of said HF, said water and said sulfolane in said stream of said HF acid catalyst are automatically controlled in response to said difference signals to provide the predetermined HF acid composition in said reactor.

5. The method of claim 4 wherein step (d) includes generating signals representative of reference and measured spectra for ASO in said HF acid catalyst, and wherein said ASO signals are processed in accordance with steps (e) through (i).

6. The method of claim 2 wherein in step (g) said derivative is normalized in accordance with:

$$D_{norm} = D_i / \sum_{2250}^{3950} |D_i|;$$

wherein
    $D_{norm}$=normalized derivative spectral element; and
    $D_i$=derivative spectral element.

7. The method of claim 1 wherein step (f) further comprises smoothing said derivative spectrum, whereby step (f) eliminates baseline shifts and low frequency variations.

8. The method of claim 1 wherein said measured spectra in step (d) is in the infrared range.

9. The method of claim 1 wherein each of the measured spectra signals generated in step (d) are in a spectral region.

10. The method of claim 4 wherein said HF alkylation system further includes an acid settler, an HF acid regenerator, a source of fresh HF acid and a source of water, wherein a stream of olefins and a stream of isobutanes are contacted in said reactor in the presence said HF acid catalyst, said reactor providing a combined hydrocarbon and HF acid output stream to said settler wherein separation provides an alkylate laden hydrocarbon product stream and a separated HF acid stream, and a minor portion of said separated HF acid stream is fed to said acid regenerator and a major portion of said separated HF acid stream is returned to said reactor along with fresh HF acid from said acid source and regenerated HF acid from said regenerator; and wherein in response to step (j):
    said HF difference signal controls the flow rate of said fresh acid from said fresh acid source to said settler, and/or the flow rate of regenerated HF acid from said regenerator to said settler;
    said water difference signal controls the flow of water from said water source to said settler; and
    said sulfolane difference signal controls the flow of sulfolane from said sulfolane source to said settler, and/or from said acid regenerator to said settler.

11. The method of claim 10 wherein step (d) includes generating signals representative of reference and measured spectra for ASO in said HF acid catalyst, and wherein said ASO signals are processed in accordance with steps (e) through (i).

12. The method of claim 1 wherein steps (i) and (j) are performed on the computer with a program.

13. A system for controlling the composition of an HF acid catalyst in a reactor of an HF alkylation system wherein said HF acid catalyst includes HF, water, ASO and an additive for reducing the vapor pressure of said HF acid catalyst, said system comprising:
    (a) means for obtaining a sample from a stream of said HF acid catalyst;
    (b) means for passing said sample to an analyzer including an attenuated total reflectance cell;
    (c) means for regulating temperature of said sample to that of a calibration standard temperature;
    (d) a computer, and program means on said computer for generating signals representative of reference and measured spectra for at least said HF, said water and said additive in said sample;
    (e) program means on said computer for processing said spectra signals to correct for instrumental variation in accordance with:

$$A_{corr} = \log_{10}\{S_o/S[R_o/R]\};$$

wherein $A_{corr}$=corrected sample absorbance spectrum;

S=current sample single beam spectrum;

$S_o$=sample single beam spectrum obtained at time 0 with an empty cell;

R=current reference cell single beam spectrum; and $R_o$=reference cell single beam spectrum obtained at time 0

(f) program means on said computer for generating a derivative of said corrected sample absorbance spectrum;

(g) program means on said computer for normalizing said derivative; in accordance with;

$$D_{norm} = D_i / \sum_{2100}^{4100} |D_i|;$$

wherein $D_{norm}$=normalized derivative spectral element;

$D_i$=derivative spectral element; and

4100–2100=spectral region, cm$^{-1}$;

(h) program means on said computer for multiplying stored model vectors by spectral elements or said normalized derivative to obtain values indicative of the amount of said HF, said water and said additive in said sample;

(i) program means on said computer for comparing said values to reference values to obtain difference signals, and (j) means for controlling the relative amounts of said HF, said water and said additive in said stream of said HF acid catalyst in response to said difference signals to provide a predetermined HF acid composition in said reactor.

14. The system of claim 13 wherein said signal generating program means includes program means for generating signals representative of reference and measured spectra for ASO in said HF acid catalyst, and wherein said ASO signals are processed by the means (e) through (i).

15. The system of claim 13 wherein the additive is sulfolane and wherein said derivative normalizing program means normalizes said derivative in accordance with:

$$D_{norm} = D_i / \sum_{2250}^{3950} |D_i|;$$

wherein $D_{norm}$=normalized derivative spectral element; and $D_i$=derivative spectral element.

16. The system of claim 13 wherein said derivative generating program means further comprises program means for smoothing said derivative spectrum, whereby baseline shifts and low frequency variations are eliminated.

17. The system of claim 13 wherein said measured spectra is in the infrared range.

18. The system of claim 13 wherein each of said spectra signals are in the same spectral region.

19. The system of claim 18 wherein the controlling means (j) includes program means on the computer.

\* \* \* \* \*